US008290582B2

United States Patent
Lin et al.

(10) Patent No.: US 8,290,582 B2
(45) Date of Patent: Oct. 16, 2012

(54) DEVICE AND METHOD TO TREAT TISSUE WITH ELECTRIC CURRENT

(75) Inventors: Bryant Lin, Menlo Park, CA (US); Tatum Tarin, Stanford, CA (US); Ross D Venook, Burlingame, CA (US); Peter Hwang, Stanford, CA (US); Richard Goode, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 777 days.

(21) Appl. No.: 12/286,126

(22) Filed: Sep. 26, 2008

(65) Prior Publication Data

US 2009/0149849 A1 Jun. 11, 2009

Related U.S. Application Data

(60) Provisional application No. 60/995,532, filed on Sep. 26, 2007.

(51) Int. Cl.
*A61N 1/00* (2006.01)
*A61B 18/18* (2006.01)

(52) U.S. Cl. ............... 607/2; 607/115; 607/134; 606/41; 128/898

(58) Field of Classification Search ............. 607/116, 607/117, 119, 133, 138, 2, 115, 113, 98, 607/99, 139, 134; 606/41, 34; 128/898
See application file for complete search history.

(56) References Cited

U.S. PATENT DOCUMENTS

| | | | |
|---|---|---|---|
| 5,190,053 A * | 3/1993 | Meer | 607/134 |
| 6,126,657 A | 10/2000 | Edwards et al. | |
| 6,152,143 A | 11/2000 | Edwards | |
| 6,159,208 A * | 12/2000 | Hovda et al. | 606/41 |
| 6,387,093 B1 | 5/2002 | Ellman et al. | |
| 6,413,254 B1 | 7/2002 | Hissong et al. | |
| 7,004,941 B2 * | 2/2006 | Tvinnereim et al. | 606/41 |
| 2001/0051783 A1 | 12/2001 | Edwards et al. | |
| 2004/0186535 A1 | 9/2004 | Knowlton et al. | |
| 2004/0206365 A1 | 10/2004 | Knowlton et al. | |
| 2004/0210214 A1 | 10/2004 | Knowlton et al. | |
| 2005/0234439 A1 | 10/2005 | Underwood | |
| 2007/0100331 A1* | 5/2007 | Young et al. | 606/41 |

* cited by examiner

*Primary Examiner* — Jackie Ho
*Assistant Examiner* — Leah Stohr
(74) *Attorney, Agent, or Firm* — Lumen Patent Firm

(57) ABSTRACT

A method of modifying properties of intrinsic tissue of an organ is provided. The method includes providing an organ, where a first electrode is disposed proximal to the organ first end. The first electrode has a surface area and insulator. A second electrode is disposed opposite the first electrode, where the organ is disposed between the first electrode and the second electrode. The second electrode has surface area and surface insulator. An organ-shaping device is provided that is disposed on the organ between the electrodes, where the organ-shaping device deforms the organ middle section along at least one lateral direction between the electrodes. An electric current is provided between the first second electrodes, where a current density gradient is provided by the electrode surface areas and the deformed organ middle section, and the properties of the intrinsic muscle tissue are modified according to the current density gradient.

17 Claims, 6 Drawing Sheets

(a)

(b) (c) (d) (e) (f)

(g) (h)

DEVICE AND METHOD TO TREAT TISSUE WITH ELECTRIC CURRENT

CROSS-REFERENCE TO RELATED APPLICATIONS

This application is cross-referenced to and claims the benefit from U.S. Provisional Patent Application 60/995,532 filed Sep. 26, 2007, which is hereby incorporated by reference.

FIELD OF THE INVENTION

The invention relates generally to altering properties inside a volume of tissue. More particularly, the invention relates to non-invasively altering the properties and anatomy of targeted tissue using electric current.

BACKGROUND

Obstructive sleep apnea (OSA) is a category of sleep-disordered breathing, which involves a disturbance of respiratory patterns during sleep. Typically, muscle tone in the body relaxes during sleep. In the throat, the airway has collapsible walls of soft tissue, which can obstruct breathing during sleep.

OSA is frequently undiagnosed, where the prevalence increases generally with age, however OSA is known to exist among African Americans, individuals with low muscle tone and soft tissue around the airway, and individuals with structural features resulting in a narrowed airway. The upper airway depends on the soft and bony tissue in the pharynx. The obstruction can occur anywhere along the naso- and oropharynx. Typically, OSA is primarily due to obstruction from the tongue falling back during sleep and occluding the airway, the soft palate laxity or a combination of both. Most OSA can be attributed to the tongue. The elderly are more likely to have OSA than young people. Men are more typical sleep apnea sufferers, however women and children are also affected.

Factors that contribute to OSA include obesity (especially neck circumference), upper airway anatomic abnormalities, smoking, and chronic nocturnal nasal congestion. Symptoms include awakening with choking or gasping, restless sleep, episodes of cessation of breathing, loud snoring, morning headaches and sleepiness during the daytime. The most serious complication is a severe form of congestive heart failure.

Sleep apnea is diagnosed with an overnight sleep study (polysomnography), which monitors patients for evaluating sleep stages, respiratory effort, airflow, arterial oxygen saturation, cardiac rate and rhythm, body position, and limb movements. Diagnosis is made with greater than 15-apneas and/or hypopneas (Apnea Hypopnea Index AHI) per hour of sleep without symptoms, or greater than 5-apneas/hypopneas per hour with symptoms. Patients with OSA, in the long term, have increased association with myocardial infarction, cerebrovascular disease, arrhythmias, and sudden cardiac death. OSA has been directly linked with systemic hypertension, pulmonary hypertension and motor vehicle accidents.

Chronic, severe obstructive sleep apnea requires treatment to prevent sleep deprivation and other complications. Some treatments involve lifestyle changes, such as avoiding alcohol or muscle relaxants, losing weight, and quitting smoking, but changing behavior is often difficult in the setting of OSA. One treatment requires sleeping at a 30-degree elevation of the upper body or higher, as if in a recliner in an attempt to prevent the gravitational collapse of the airway. Another treatment is the use of a continuous positive air pressure (CPAP) machine.

The CPAP machine delivers a stream of compressed air via a hose to a nasal pillow, nose mask or full-face mask, keeping the airway open under air pressure so that unobstructed breathing becomes possible, reducing and/or preventing apneas and hypopneas. However, a significant number of patients cannot tolerate CPAP because of the mask, noise, sensation of airflow, and dry mucosa from the airflow. Oral appliances have been used to hold the tongue or advance the mandible and so directly effect causes of obstruction. These appliances have been shown to improve OSA but they are poorly tolerated. Oral appliances are also thought to be less effective than CPAP.

There are also invasive surgical procedures to remove and tighten tissue, and to widen the airway. Uvulopalatopharyngoplasty (UPPP), palate support pillars, Radiofrequency (RF) ablation (Gyrus ENT), tongue suspension, genioglossus advancement, and maxillary-mandibular advancement have all been tried with variable success. Genioglossus and maxillary-mandibular advancement is very effective but invasive and uncomfortable often leading to changes in facial appearance and speech. UPPP can be effective in a subset of patients and is often used in conjunction with other treatments. Tongue suspension (Repose) is effective in the short term but loses efficacy after one year. Palate support pillars are also useful in only a limited subset of patients. Radiofrequency ablation has great promise in the past but comfort and efficacy have been limited due to the need to deliver RF current at multiple sites over several separate procedures using a painful needle. In conventional RF ablation configurations, the current density is highest at the ablation electrode. The ohmic heating occurs at the tissue-electrode interface and then the heat is transferred to the surrounding tissue through thermal conduction. In order to ablate (and therefore debulk and stiffen) the tongue, the Gyrus device uses ablation "needles" to penetrate and deliver energy to the tongue's interior. If the RF current, using a conventional setup, is delivered from the tongue's surface, the patient receives painful burns on the surface of the tongue before getting significant heating and debulking of the organ. Even with extensive surface cooling at the electrode interface, surface burns can occur in order to achieve interior target temperatures.

What is needed is a comfortable, minimally invasive and effective long-term device and method to non-invasively change the properties inside a volume of tissue, especially the tongue to treat obstructive sleep apnea.

SUMMARY OF THE INVENTION

To address the current need in the art, a method of modifying properties of intrinsic tissue of an organ is provided. The method includes providing an organ having a first end, a middle section and a second end, where a first electrode is disposed proximal to the organ first end. The first electrode includes a first electrode surface area and a first electrode surface insulator. A second electrode is disposed opposite the first electrode, where part of the organ is disposed between the first electrode and the second electrode. The second electrode includes a second electrode surface area and a second electrode surface insulator. An organ-shaping device is provided that is disposed on the organ between the electrodes, where the organ-shaping device deforms the organ middle section along at least one lateral direction between the electrodes. An electric current is provided between the first electrode and the second electrode, where a current density gradient is provided by the electrode surface areas and the deformed organ middle section, and the properties of the intrinsic muscle tissue are modified according to the current density gradient.

In one aspect of the invention, the organ can include a tongue, a heart, skin, fat underlying the skin, connective tissue underlying the skin, uterus, uterus neck, small intestines, colon, stomach, esophagus, muscle, vessel, tonsil, lymphatic/adenoid tissue, tumor, hemorrhoids, kidney, bladder, ureter, urethra, prostate, ovaries, vas deferens, neurologic tissue or fallopian tubes.

In another aspect of the invention, the electrode surface area can be within a range of 1 mm$^2$ to 2,500 cm$^2$.

In a further aspect, the insulator is disposed to insulate all or some of the electrode.

In yet another aspect, the insulator is disposed to insulate tissue.

In another aspect of the invention, the insulator is disposed to control a current path, where the insulator eliminates or reduces current leakage up to a deformation point imposed by the organ-shaping device.

In one aspect, the electrode further includes a shape that can be a square, a rectangle, a circle, an oval, a line, a point, a parallelogram or an irregular shape, where the irregular shape is defined by an object under treatment.

According to one aspect, the organ-shaping device can be a clamp, a cinch, tongs, a tube a strap, a strip of nonconductive material, a suture, staples, human hands or pins.

In another aspect of the invention, the shaping device has at least one shaping surface that can include a plane surface, a concave surface, a convex surface, a surface having a single apex, a surface having multiple apecies, a surface having multiple curves, angulated surfaces or a zig-zag surface.

According to one aspect, the electric power has an ablation power range of 1 to 100 Watts.

In another aspect, the gradient can be linear, symmetric linear, asymmetric linear, non-linear, symmetric non-linear, asymmetric non-linear gradient, symmetric wave, asymmetric wave, symmetric saw tooth, or asymmetric saw tooth.

In one aspect, the invention further includes providing a cooling element, where the cooling element can be incorporated to a deformation point, the organ-shaping device, the electrode, a path of the current or surrounding tissue.

In another aspect of the invention, the modification of the intrinsic muscle tissue of the organ includes modifying a tissue in regions that include a tongue, a palate, a tonsil, a turbinate or a uvula, whereby a sleep disorder is treated. According to one aspect, the second electrode is disposed on exterior skin, where the exterior skin is proximal to a geniohyoideus region of the tongue organ, or anywhere on a body that provides the organ between the electrodes. In a further aspect, the first electrode insulator is disposed to insulate a mouth region holding the tongue organ, where the electrode includes an un-insulated region in contact with a surface of the tongue organ, where a dorsum region of the tongue organ is modified according to the current density gradient.

In a further aspect of the invention, the properties of the intrinsic muscle tissue of the organ can include stiffness, elasticity, density, mass, or water content.

In yet another aspect of the invention, the tissue is modified by ohmic heating, where the heating induces cell death to promote scaring, fibrosis and volume reduction.

In a further aspect of the invention, the current modifies an architecture of the collagen in the organ.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The current invention includes non-invasive methods and devices to modify tissue using RF current. RF current heats tissue through ohmic heating at areas of high current concentration. With RF current delivered from the surface of the organ, such as the tongue, the invention enables heating within the tongue without creating surface burns. The invention provides a temperature gradient from the interior to the exterior of the target area of the organ. The organ can include a tongue, a heart, skin, fat underlying the skin, connective tissue underlying the skin, uterus, uterus neck, small intestines, colon, stomach, esophagus, muscle, vessel, tonsil, lymphatic/adenoid tissue, tumor, hemorrhoids, kidney, bladder, ureter, urethra, prostate, ovaries, or fallopian tubes.

In one embodiment of the invention, tissue properties are changed in the tongue, to treat obstructive sleep apnea. The treatment includes delivering an electrical current profile to the tongue to induce changes that can include the stiffness, elasticity and bulk (volume and/or weight).

Because heating from RF ablation is due to ohmic heating, which occurs fastest at the point of highest current density (assuming relative uniformity of tissue impedance), the current invention causes maximum heating of a select volume of tissue that is separated by a predetermined distance from the tissue-electrode interfaces. The tissue of an organ is shaped and insulated. The applied current runs through a narrowed area ("bottleneck" or "waist"), where the current density increases relative to the surrounding tissue and a relative maximum heating will occur at the narrowed area.

Figure 1:
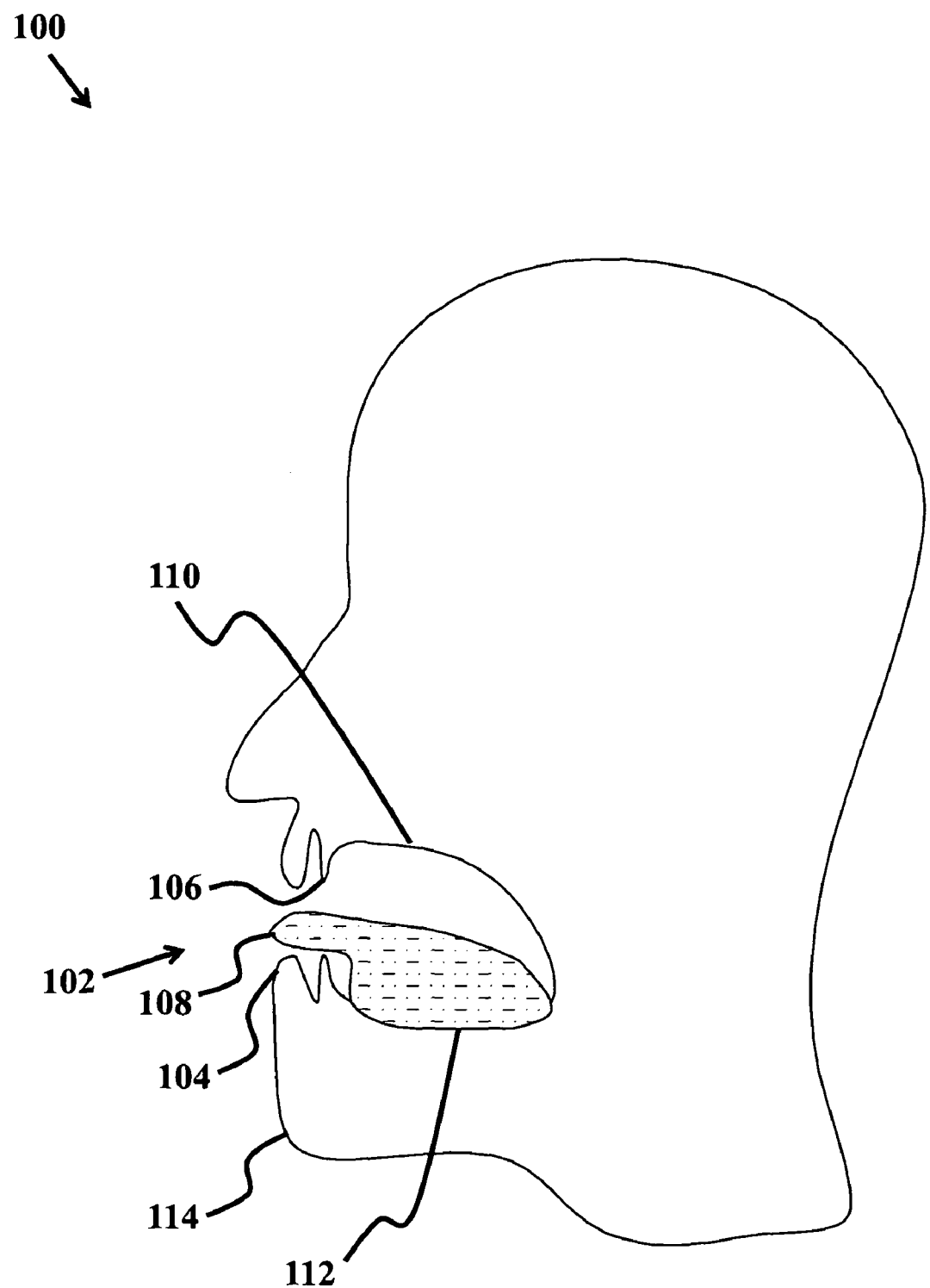
FIG. 1 shows a planar cutaway view of a patient.

Referring now to the drawings, FIG. 1 shows a planar cutaway view of a head of a patient 100, where shown is the patient's open mouth 102 that includes the lips 104, teeth 106, a tongue 108, a mouth roof 110, a mouth floor 112 and a chin 114.

Figure 2:
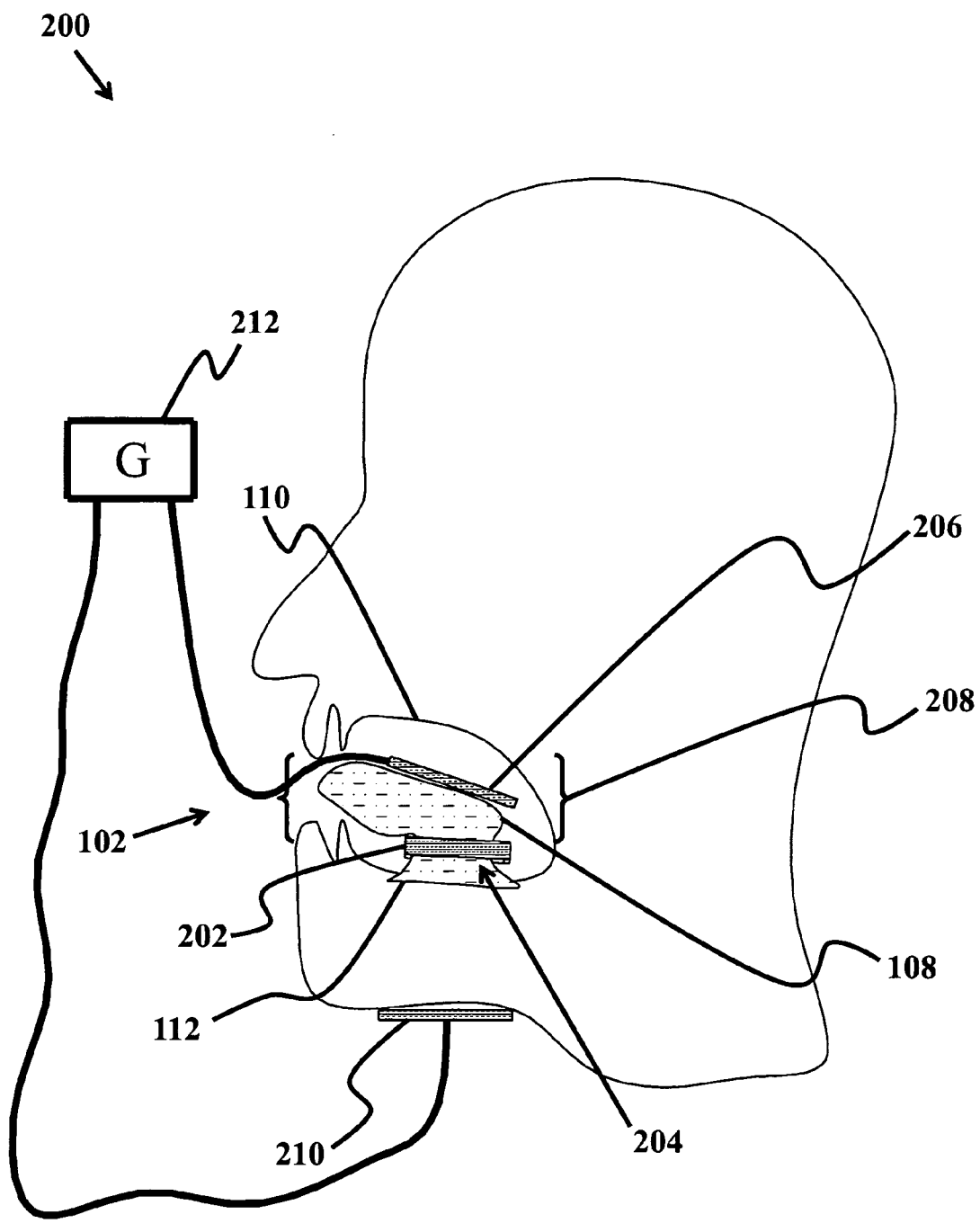
FIG. 2 shows a planar cutaway view of a patient prepared for treatment according to the present invention.

FIG. 2 shows the patient 100 prepared for treatment 200 according to one embodiment of the invention. An organ-shaping device 202 deforms the tongue 108 in a plane that is offset from the floor of the mouth 112, whereby a deformation point 204 is formed. The organ-shaping device 202 can be a clamp, a cinch, tongs, a tube a strap, a strip of nonconductive material, a suture, staples, or pins. A first electrode 206 is applied to the upper (anterior) region 208 (shown between brackets) of the tongue 108, that spans from the organ-shaping device 202 to the tip of the tongue 108, is electrically insulated (not shown) from the rest of the mouth 102. A second electrode 210 is shown affixed below the chin 114, however the second electrode may be affixed anywhere on the body (see FIG. 4) so as to dispose the organ under treatment between the first and second electrodes. A power generator 212 provides a current between the two electrodes (206/208). The generator 212 may provide alternating sinusoidal power, direct current (DC), square wave, saw tooth wave, or other waveforms. The generator 212 may be temperature controlled, impedance controlled, voltage controlled, current controlled or controlled by another measurable property of electricity or tissue. The frequency range of the provided power could be from 1 Hz to 1 GHz.

Figure 3:
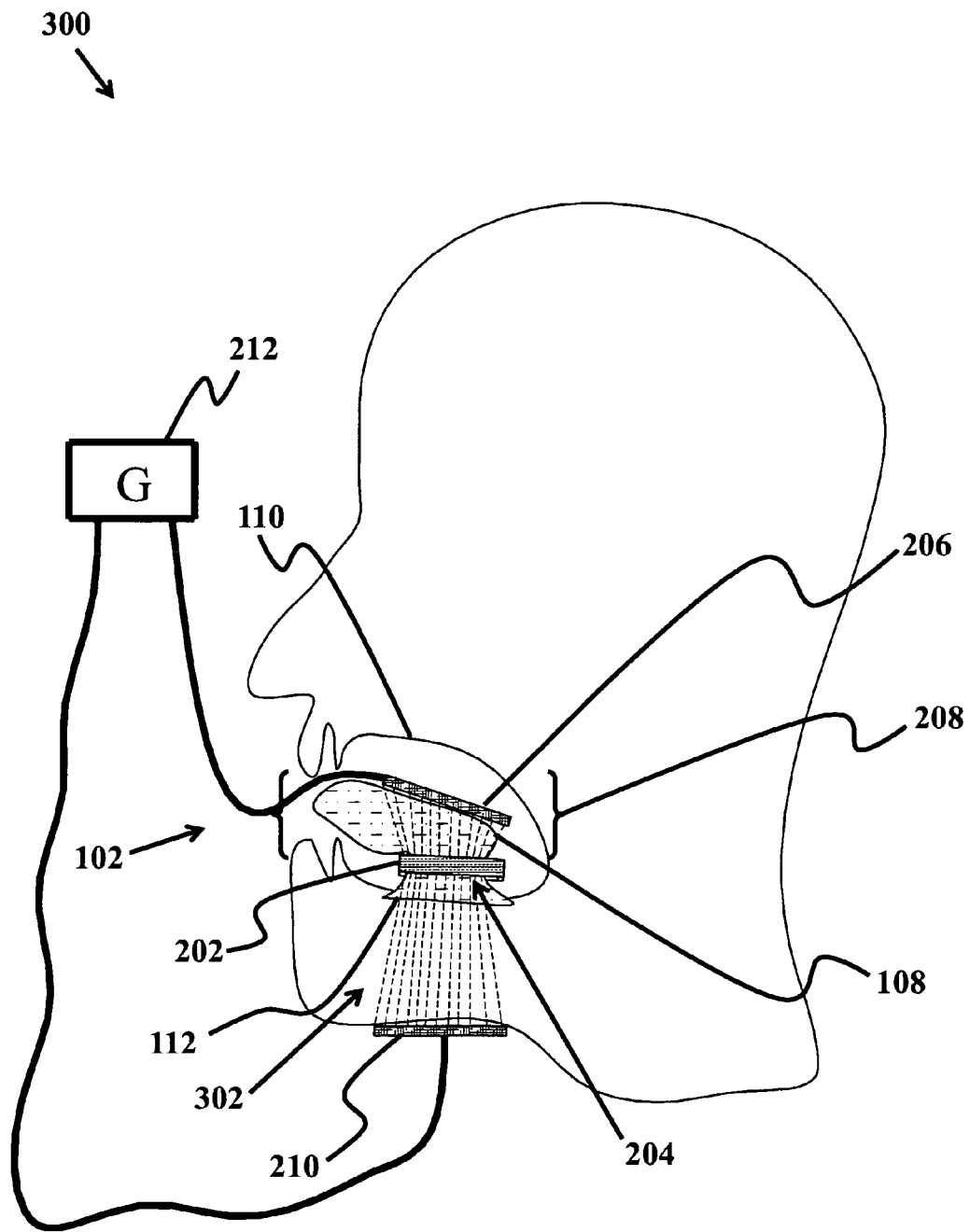
FIG. 3 shows a planar cutaway view of a patient during treatment according to the present invention.
Figure 6:
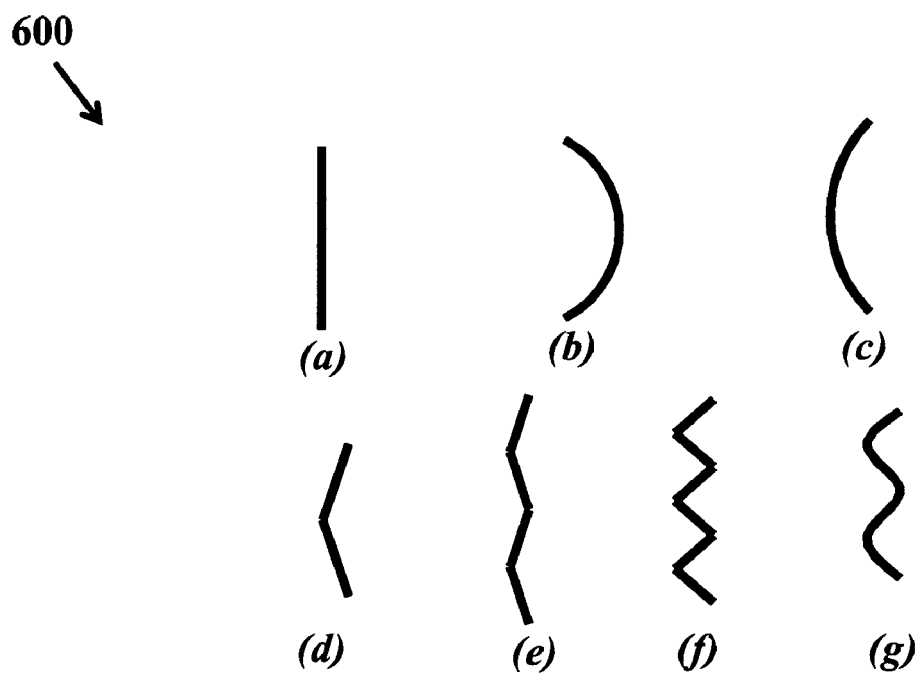
FIGS. 6a-6g show cross-section views of some exemplary organ-shaping device surface profiles according to the present invention.
Figure 7:
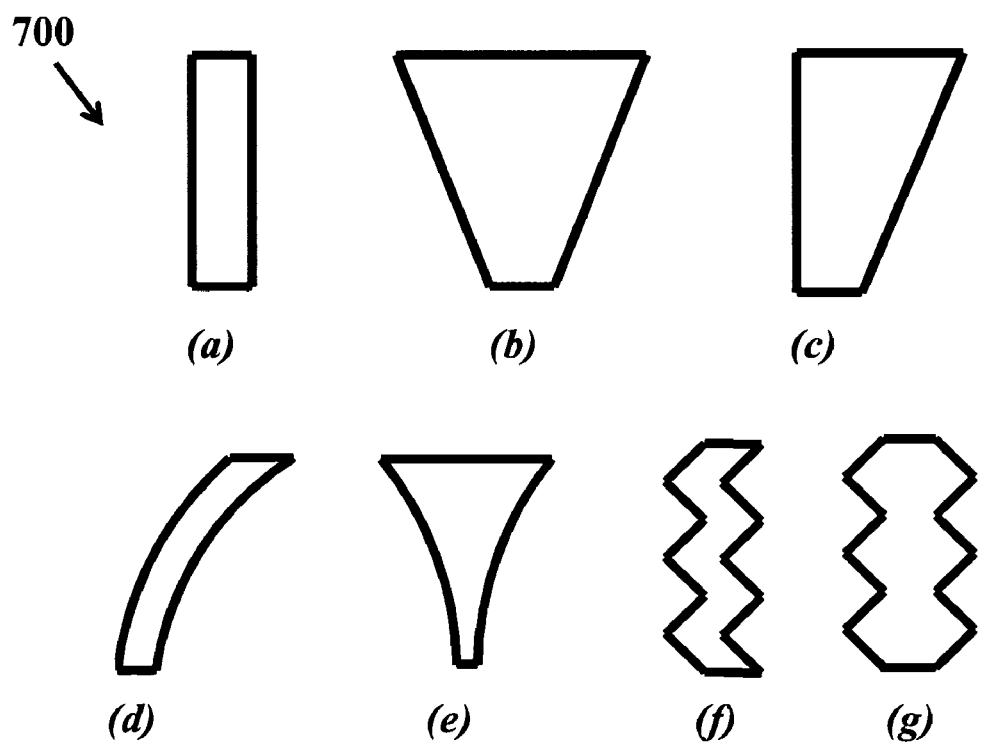
FIG. 7a-7g show cross-section views of some exemplary profiles of current gradients according to the present invention.

FIG. 3 shows the patient 100 during treatment 300 according to one embodiment of the invention. When current 302 is applied between the electrodes (206/210), heating occurs at the narrowing point 204 because the current density is highest at that location. The electric power can have an ablation power range of 1 to 100 Watts. The current may be modulated, pulsed or constant. The heating of the organ occurs internally first at the narrowing point 204 and spreads outwards thereby causing non-invasive heating at a desired internal location. The narrowing may be shaped (see FIG. 6) to control the heating, where a decrease in cross-sectional area will cause an increase in current density. Cooling may not be necessary but can further control shaping of the desired heat profile. Cooling may be applied (not shown) at the first electrode 204, second electrode 208, the deformation point 204 and/or anywhere along current path 302 to also shape the desired heating profile. The modification of the intrinsic muscle tissue of the organ includes modifying tissue in regions that can include a tongue, a palate, a tonsil, a turbinate or a uvula, whereby a sleep disorder is treated. The second electrode can be disposed on exterior skin, where the exterior skin is proximal to a genio-hyoideus region of the tongue organ, or anywhere on a body that provides the organ between the electrodes (see FIG. 4). The resultant modified properties of the intrinsic muscle tissue of the organ can include stiffness, elasticity, density, mass, or water content, where the tissue is modified by heating to induce cell death to promote scaring, fibrosis and volume reduction.

Figure 4:
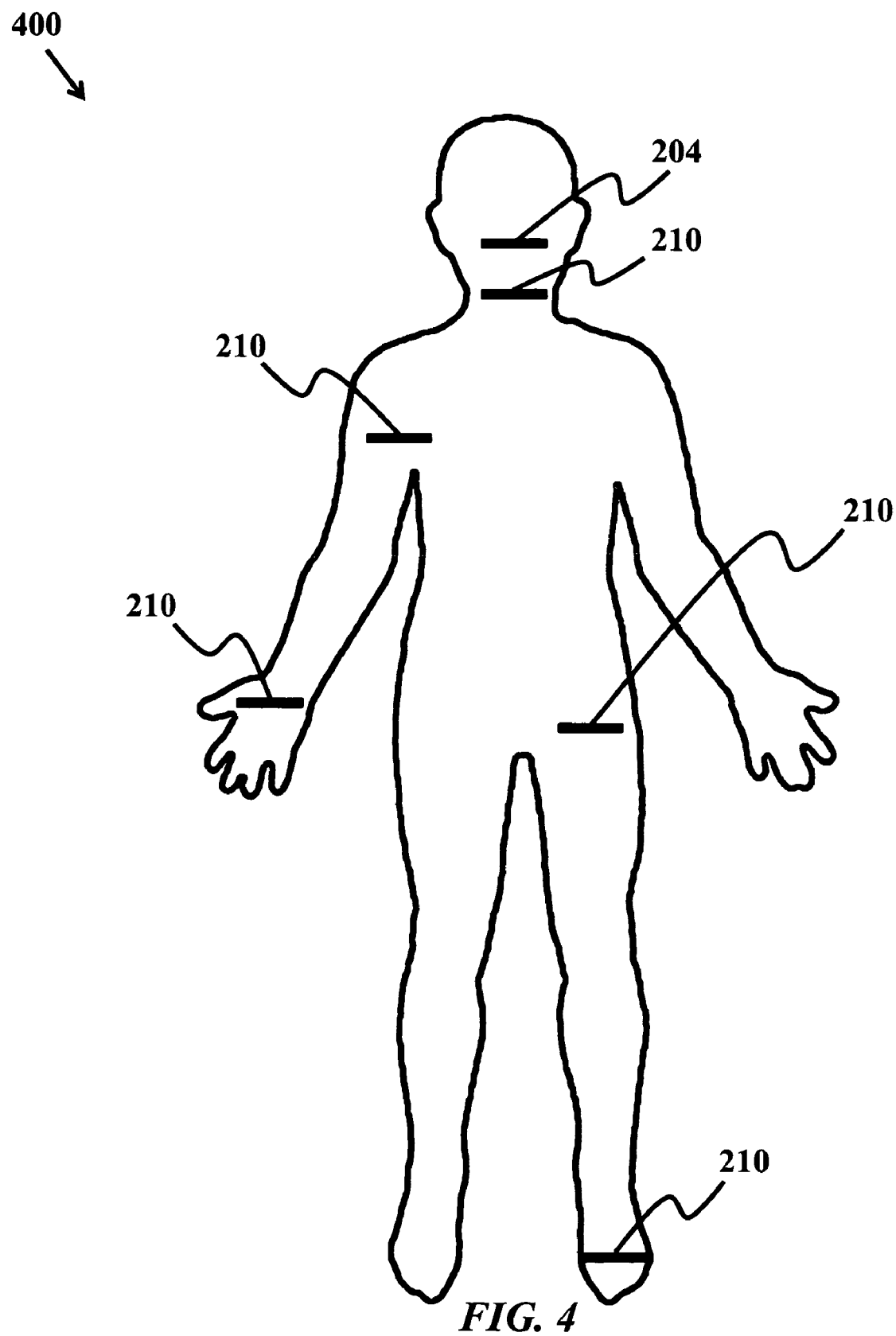
FIG. 4 shows a schematic view of different electrode placements according to the present invention.

FIG. 4 shows a schematic view of different electrode placements 400 on a patient according to the current invention. As shown, the first electrode 204 is in positioned in the mouth region as described above. The second electrode 210 may be placed anywhere on the body, where the organ under treatment is disposed between the two electrodes (204/210).

Figure 5:
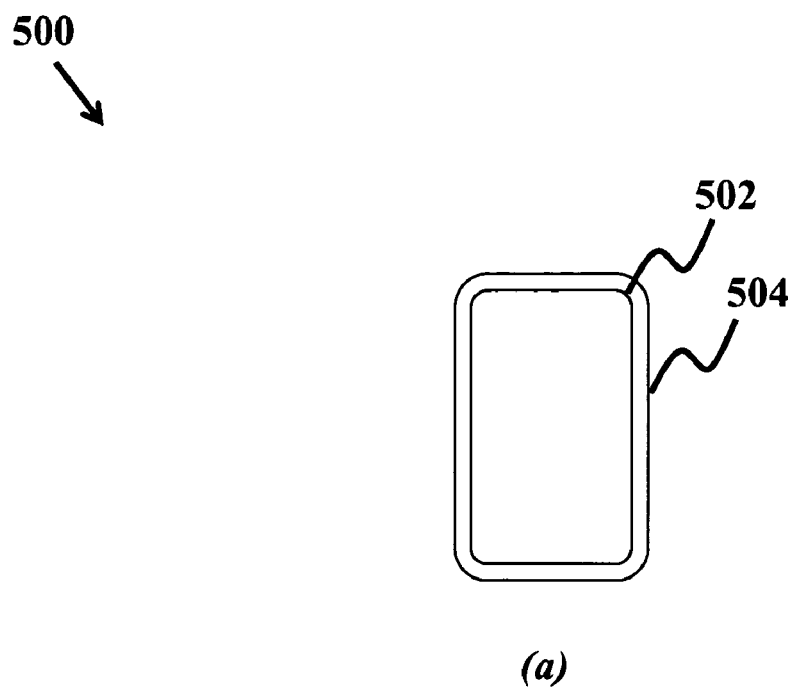
FIGS. 5a-5h show top views of some exemplary electrode profiles according to the present invention.
Figure 5:
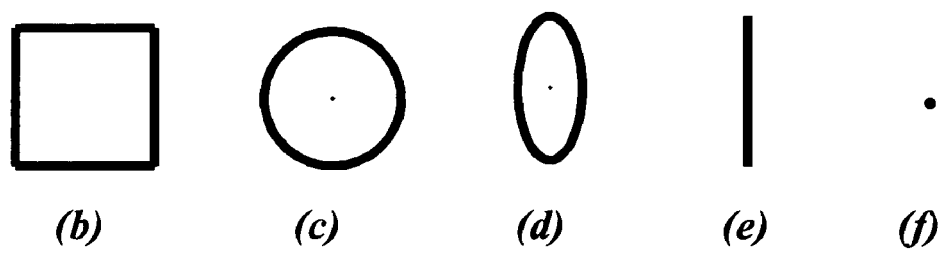
Figure 5:
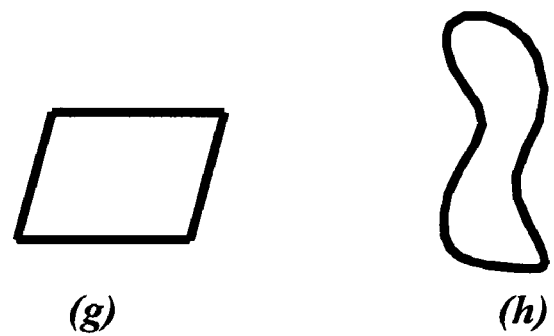

FIGS. 5a-5h show top views of some exemplary electrode profiles 500. FIG. 5a shows a rectangular electrode 502 having at least part of which is insulated 504, which is implied for all possible electrode shapes. The insulator can be disposed to insulate all or some of the electrode, disposed to insulate tissue, or disposed to control a current path, where the insulator ensures no current leakage up to a deformation point. The first electrode insulator can be disposed to insulate the mouth region holding the tongue organ, where the electrode includes an un-insulated region in contact with a surface of the tongue organ, whereby a dorsum region of the tongue is modified according to the current density gradient. The electrode surface area can be within a range of 1 mm$^2$ to 2,500 cm$^2$. The electrode shapes can also be a square (FIG. 5b), a circle (FIG. 5c), an oval (FIG. 5d), a line (FIG. 5e), a point (FIG. 5f), a parallelogram (FIG. 5g) or an irregular shape (FIG. 5h), where the irregular shape of the electrode profile can be defined by the organ being treated.

FIGS. 6a-6g show cross-section views of some exemplary organ-shaping device surface profiles 600. The organ-shaping device surface can include a plane surface (FIG. 6a), where the planar surface can be angulated, a concave surface (FIG. 6b), a convex surface (FIG. 6c), a surface having a single apex (FIG. 6d), a surface having multiple apex (FIG. 6e), where each apex may be at a different depth or incline, a zig-zag surface (FIG. 6f), or a surface having multiple curves (FIG. 6g), where the curves may be at different depths or curvatures.

FIGS. 7a-7g show cross-section views of some exemplary profiles of current gradients 700 formed by the electrode profiles 500, organ-shaping device profiles 600 and electrode separation among others. The gradient 700 can be linear (FIG. 7a), symmetric linear (FIG. 7b), asymmetric linear (FIG. 7c), non-linear such as symmetric non-linear (FIG. 7d) or asymmetric non-linear (FIG. e), symmetric saw tooth (FIG. 7f), or asymmetric saw tooth (FIG. 7g), where the saw tooth can include symmetric wave and asymmetric wave (not shown).

The current invention is not limited to sleep apnea treatment applications, other applications include, but are not limited to, use in the heart to treat arrhythmias, use in cancerous tissue, use in connective tissue and fat for aesthetic treatment, or use for shaping tissue.

This method of directing of shaping applied current could be done non-invasively, minimally-invasively, or invasively, and it could be applied to any type or types of tissue. In the aesthetic device market, this invention would be useful. In one embodiment, a shaping apparatus is used to cause a narrow point in loose neck or abdominal skin and fat. RF current is applied and subcutaneous or adipose tissue is heated shrinking and tightening the area to achieve a cosmetic effect noninvasively by heating underneath the surface of the skin without causing pain and heat to the surface.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art.

All such variations are considered to be within the scope and spirit of the present invention as defined by the following claims and their legal equivalents.

What is claimed:

1. A method of modifying properties of intrinsic tissue of an organ comprising:
   a. providing an organ, wherein said organ comprises an organ first end, an organ middle section and an organ second end;
   b. providing a first electrode disposed proximal to said organ first end, wherein said first electrode comprises a first electrode surface area;
   c. providing a second electrode disposed opposite said first electrode, wherein said organ is disposed between said first electrode and said second electrode, wherein said second electrode is disposed on exterior skin;
   d. providing an organ-shaping device, wherein said organ-shaping device is disposed on said organ between said electrodes, wherein said organ-shaping device deforms said organ middle section along at least one lateral direction between said electrodes; and
   e. providing an electric current between said first electrode and said second electrode, wherein a current density gradient is provided by said electrode surface areas and said deformed organ middle section, wherein said properties of said intrinsic tissue is modified according to said current density gradient.

2. The method according to claim 1, wherein said organ is selected from a group consisting of a tongue, a heart, skin, lung, fat underlying said skin, connective tissue underlying said skin, uterus, uterus neck, small intestines, colon, stomach, esophagus, cartilage, muscle, bone, vessel, tonsil, lymphatic/adenoid tissue, tumor, hemorrhoids, kidney, bladder, ureter, urethra, prostate, ovaries, vas deferens, neurologic tissue, and fallopian tubes.

3. The method of claim 1, wherein said electrode surface area comprises an area within a range of 1 mm$^2$ to 2,500 cm$^2$.

4. The method of claim 1, wherein an insulator is disposed to insulate all or some of said electrode.

5. The method of claim 1, wherein an insulator is disposed to insulate tissue.

6. The method of claim 1, wherein an insulator is disposed to control a current path, wherein said insulator eliminates or reduces current leakage up to a deformation point, wherein said deformation point is imposed by said organ-shaping device.

7. The method of claim 1, wherein said electrode further comprises a shape, wherein said shape is selected from a group consisting of a square, a rectangle, a circle, an oval, a line, a point, a parallelogram and an irregular shape, wherein said irregular shape is defined by an object under treatment.

8. The method of claim 1, wherein said organ-shaping device is selected from a group consisting of a clamp, a cinch, tongs, a tube a strap, a strip of nonconductive material, a suture, staples, human hands and pins.

9. The method of claim 1, wherein said shaping device comprises at least one shaping surface, wherein said at least one shaping surface is selected from a group consisting of a plane surface, a concave surface, a convex surface, a surface having a single apex, and a surface having multiple said apices, a surface having multiple curves, angulated surfaces and a zig-zag surface.

10. The method of claim 1, wherein said electric current comprises an ablation power, where said ablation power is in a range of 1 to 100 Watts.

11. The method of claim 1, wherein said gradient is selected from a group consisting of linear, symmetric linear, asymmetric linear, non-linear, symmetric non-linear, asymmetric non-linear gradient, symmetric wave, asymmetric wave, symmetric saw tooth, and asymmetric saw tooth.

12. The method of claim 1, wherein said modification of said intrinsic tissue of said organ comprises modifying a tissue in regions selected from a group consisting of a tongue, a palate, a tonsil, a turbinate and a uvula, whereby a sleep disorder is treated.

13. The method of claim 1, wherein said first electrode comprises an insulator disposed to insulate a mouth region holding said tongue organ, wherein said electrode comprises an uninsulated region in contact with a surface of said tongue organ, wherein a dorsum region of said tongue organ is modified according to said current density gradient.

14. The method of claim 1, wherein said exterior skin is proximal to a genio-hyoideus region of a tongue organ, or anywhere on a body that provides said tissue between said electrodes.

15. The method of claim 1, wherein said property of said tissue of said organ is selected from a group consisting of stiffness, elasticity, density, mass, and water content.

16. The method of claim 1, wherein tissue is modified by ohmic heating, wherein said heating induces cell death to promote scaring, fibrosis and volume reduction.

17. The method of claim 1, wherein said current modifies an architecture of collagen in said organ.

\* \* \* \* \*